US009795636B2

(12) United States Patent
Oda et al.

(10) Patent No.: US 9,795,636 B2
(45) Date of Patent: *Oct. 24, 2017

(54) STABLE BICARBONATE ION-CONTAINING DRUG SOLUTION

(71) Applicants: NATIONAL UNIVERSITY CORPORATION CHIBA UNIVERSITY, Chiba-shi, Chiba (JP); FUSO PHARMACEUTICAL INDUSTRIES, LTD., Osaka-shi, Osaka (JP)

(72) Inventors: Shigeto Oda, Chiba (JP); Tomohito Sadahiro, Chiba (JP); Masataka Nakamura, Chiba (JP); Syuichi Tanaka, Osaka (JP); Shogo Tokuoka, Osaka (JP); Hiroya Otani, Osaka (JP)

(73) Assignees: NATIONAL UNIVERSITY CORPORATION CHIBA UNIVERSITY, Chiba (JP); FUSO PHARMACEUTICAL INDUSTRIES, LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/272,026

(22) Filed: May 7, 2014

(65) Prior Publication Data
US 2014/0335198 A1 Nov. 13, 2014

Related U.S. Application Data

(63) Continuation of application No. 12/680,857, filed as application No. PCT/JP2008/068192 on Oct. 6, 2008, now Pat. No. 8,771,749.

(30) Foreign Application Priority Data

Oct. 5, 2007 (JP) ................. 2007-262551

(51) Int. Cl.
| | | |
|---|---|---|
| *A61K 33/42* | (2006.01) | |
| *A61K 31/7004* | (2006.01) | |
| *A61K 33/06* | (2006.01) | |
| *A61K 33/14* | (2006.01) | |
| *A61K 45/06* | (2006.01) | |
| *A61K 47/02* | (2006.01) | |
| *A61K 47/26* | (2006.01) | |
| *A61K 9/00* | (2006.01) | |
| *A61K 9/08* | (2006.01) | |
| *A61K 33/10* | (2006.01) | |
| *A61M 1/16* | (2006.01) | |
| *B65D 81/32* | (2006.01) | |

(52) U.S. Cl.
CPC ............ *A61K 33/42* (2013.01); *A61K 9/0019* (2013.01); *A61K 9/08* (2013.01); *A61K 31/7004* (2013.01); *A61K 33/06* (2013.01); *A61K 33/10* (2013.01); *A61K 33/14* (2013.01); *A61K 45/06* (2013.01); *A61K 47/02* (2013.01); *A61K 47/26* (2013.01); *A61M 1/1654* (2013.01); *B65D 81/3261* (2013.01)

(58) Field of Classification Search
CPC ................ A61K 2300/00; A61K 33/14; A61K 31/7004; A61K 33/00; A61K 33/42; A61K 31/19; A61K 31/70; A61K 31/718; A61K 35/14; A61K 31/194; A61K 33/06; A61K 33/10; A61K 9/08; A61K 31/66; A61K 9/0019
See application file for complete search history.

(56) References Cited

U.S. PATENT DOCUMENTS

| | | | | |
|---|---|---|---|---|
| 4,403,992 | A * | 9/1983 | Bertellini | A61J 1/10 604/262 |
| 5,616,248 | A * | 4/1997 | Schal | A61K 33/14 210/646 |
| 2004/0018966 | A1 * | 1/2004 | Segall | A01N 1/02 604/506 |
| 2004/0022816 | A1 | 2/2004 | Hollander | |

(Continued)

FOREIGN PATENT DOCUMENTS

| | | |
|---|---|---|
| CN | 1857311 | 11/2006 |
| EP | 1854492 | 11/2007 |

(Continued)

OTHER PUBLICATIONS

Katayama et al. "High flow CHDF, High volume CHF". *Emergency and Critical Care*, vol. 18, No. 1-2, pp. 224-228 (2006) and partial English translation.

Moriguchi et al. "The recent progress in blood purification in critical care: overview". *Japanese Journal of Clinical Medicine*, vol. 62, pp. 397-402 (2004) and partial English translation.

(Continued)

*Primary Examiner* — Audrea Buckley
(74) *Attorney, Agent, or Firm* — Hamre, Schumann, Mueller & Larson, P.C.

(57) ABSTRACT

The invention relates to a stable bicarbonate ion-containing drug solution, particularly a bicarbonate-containing drug solution for dialysis in which the stability has been improved by the presence of a phosphate ion. Further, the invention relates to a drug solution for acute blood purification, particularly a dialysate and a substitution liquid for acute blood purification to be mixed before use containing the drug solution. Still further, the invention relates to a dialysate and a substitution liquid for acute blood purification to be mixed before use in which the formation of insoluble fine particles or precipitates is prevented for a long time after mixing and with which hypokalemeia and hypophosphatemia are not caused.

8 Claims, 1 Drawing Sheet

(56) References Cited

U.S. PATENT DOCUMENTS

| | | | |
|---|---|---|---|
| 2005/0220889 A1* | 10/2005 | Charmot | A61K 9/5026 424/490 |
| 2006/0154873 A1* | 7/2006 | Sumiyoshi | A61J 1/2093 514/23 |
| 2007/0148258 A1 | 6/2007 | O'Neill et al. | |
| 2007/0265593 A1* | 11/2007 | Kitagawa | A61J 1/05 604/403 |
| 2008/0085325 A1 | 4/2008 | Carlsson et al. | |

FOREIGN PATENT DOCUMENTS

| | | |
|---|---|---|
| JP | 2003-104869 | 4/2003 |
| JP | 2005-28108 | 2/2005 |
| JP | 2007-523056 | 8/2007 |
| JP | 2008-264508 | 11/2008 |
| WO | WO 83/00293 | 2/1983 |
| WO | WO 02/24209 | 3/2002 |
| WO | WO 2006/041409 | 4/2006 |

OTHER PUBLICATIONS

Hastings et al. "Studies on the solubility of calcium salts. I. The solubility of calcium carbonate in salt solutions and biological fluids". *The Journal Biological Chemistry*, vol. 71, No. 3, pp. 723-181 (1927).

Ing et al.: "Increasing plasma phosphorus values by enriching with phosphorus the "acid concentrate" of a bicarbonate-buffered dialysate delivery system"; International Journal of Artificial Organs, Milan, IT, vol. 15, No. 12, pp. 701-703 (Jan. 1, 1992).

Ing et al., "Phosphorus-Enriched Hemodialysates: Formulations and Clinical Use", Hemodialysis International, vol. 7, No. 2, 2003, pp. 148-155, 8 pages provided.

Troyanov S et al., "Phosphate addition to hemodiafiltration solutions during continuous renal replacement therapy.", Intensive Care Med, vol. 30, No. 8, Aug. 2004, Epub May 20, 2004, pp. 1662-1665, 4 pages provided.

Anonymous "Reference Ranges and Conversion Factors", UCSD Lab Medicine, Apr. 5, 2010, pp. 1-5.

Office Action of European Patent Application No. 08835962.5, dated Jun. 21, 2017, 7 pages provded.

* cited by examiner

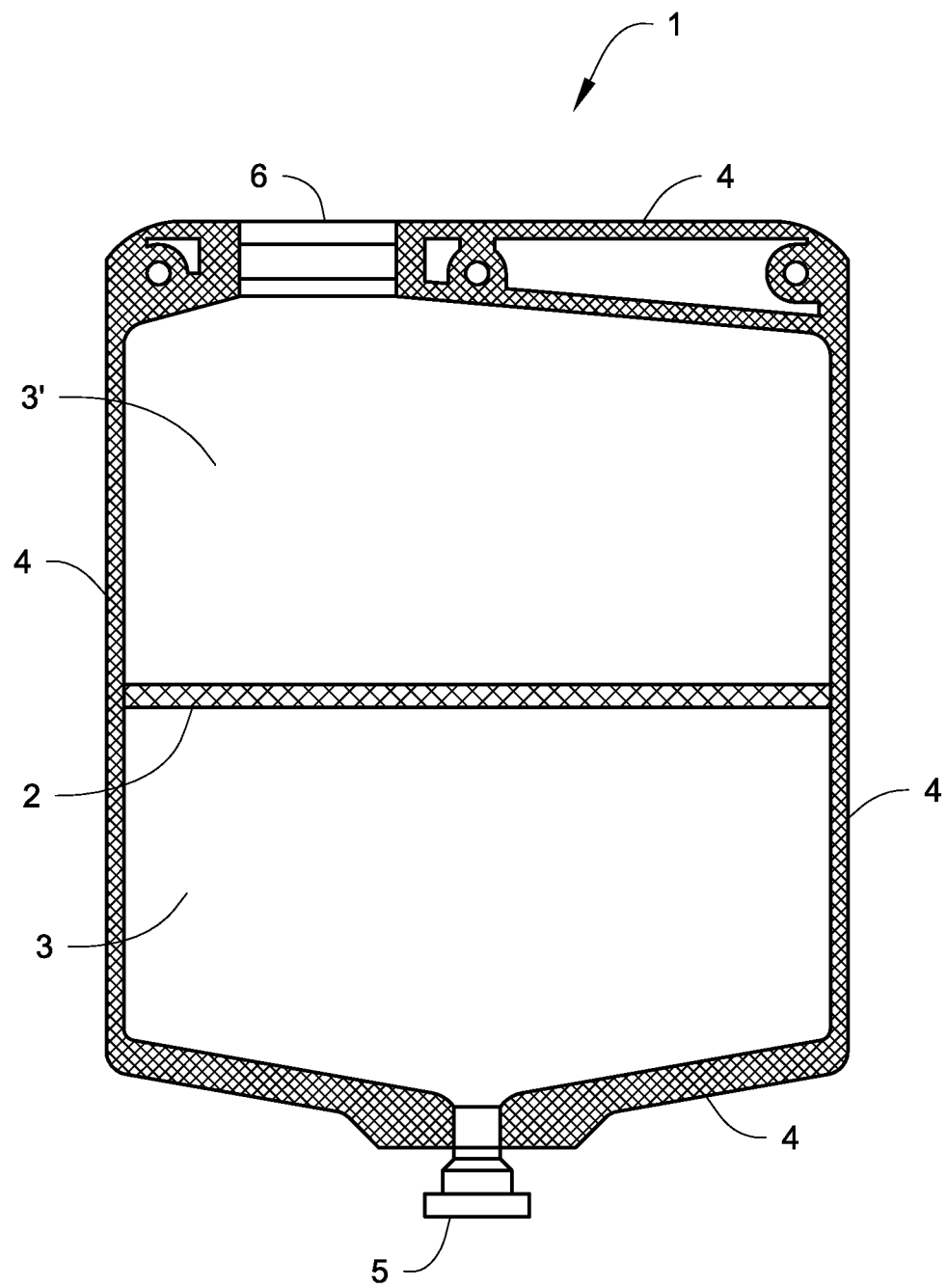

STABLE BICARBONATE ION-CONTAINING DRUG SOLUTION

This application is a Continuation of U.S. Ser. No. 12/680,857 filed May 4, 2010, which is a National Stage Application of PCT/JP2008/068192, filed Oct. 6, 2008, which applications are incorporated herein by reference.

TECHNICAL FIELD

The present invention relates to a stable bicarbonate ion-containing drug solution, particularly a bicarbonate-containing drug solution for dialysis, of which the stability is improved by the presence of phosphate ion. Also, it relates to a drug solution for acute blood purification (i.e. blood purification in critical care), particularly a dialysate or substitution liquid for acute blood purification of mixing type on use, comprising said bicarbonate ion-containing drug solution. Further, it relates to a dialysate or substitution liquid for acute blood purification of mixing type on use, which is prevented from the formation of insoluble fine particles or precipitates for a long time after mixing and does not cause hypokalemia and hypophosphatemia.

BACKGROUND ART

Homeostasis of a body fluid is significantly impaired by the rapid accumulation of toxins or pathogens from diseases such as acute cardiac failure, acute renal failure, acute hepatic failure, postoperative hepatic failure, sepsis, burn, toxicosis, fulminant hepatitis and acute pancreatitis. For treatment of the exacerbation of such acute or chronic diseases, the acute blood purification therapy is applied thereto, because it is required to purify the blood and/or body fluid urgently so as to maintain the homeostasis and ameliorate the pathological condition.

The acute blood purification therapy is a blood purification method experientially developed mainly in the critical care/intensive care field, which removes unnecessary or toxic substances from bloods by dialysis, filtration, adsorption or separation (Non-Patent Reference 1).

A specific method for the acute blood purification therapy comprises blood purification by an extracorporeal circulation of blood such as continuous hemodialysis (CHD), continuous hemofiltration (CHF), continuous hemodiafiltration (CHDF), hemodialysis (HD), hemoadsorption (HA), plasma adsorption (PA), plasma exchange (PE) or leukocytapheresis (LC). In these days, CHDF and PE are predominant due to the expansion of their application, the progress of the pathology resolution, etc. (Non-Patent Reference 2).

In the acute blood purification therapy, the use of a huge volume of dialysate or substitution liquid is required for removal of detrimental substances by utilization of the principle of diffusion, ultrafiltration, microfiltration, adsorption or the like.

The essential requirements for the dialysate or substitution liquid to be used in the acute blood purification therapy are as follows: (1) unnecessary or surplus substances are reduced; (2) essential or insufficient substances are supplemented; (3) detrimental substances are undetectable or low enough to cause no problem; (4) essential substances in a body are not reduced below normal concentrations; (5) metabolic substances taken up into a body are not so much as causing a burden to the metabolic pathway; (6) osmotic pressure is close to that of blood; (7) stability is kept and handling is easy, etc. As the dialysate or substitution liquid presently used in the acute blood purification therapy, there are exemplified dialysates for artificial kidneys (e.g. Kindaly®Solution: Fuso Pharmaceutical Industries, Inc.) and substitution liquids for filtration type artificial kidneys (e.g. Sublood®-B, Sublood®-BS: Fuso Pharmaceutical Industries, Inc.) which are sold in the market for the therapy of chronic renal failure, because those meet said requirements and are easily available.

Many of these dialysates and substitution liquids contain sodium bicarbonate. Therefore, the reaction of calcium and magnesium ions with bicarbonate ion therein proceeds with the lapse of time to form insoluble fine particles or precipitates of carbonates. In order to avoid this problem, those are supplied as a kit formulation comprising a solution containing calcium ion ($Ca^{2+}$) and magnesium ion ($Mg^{2+}$) (hereinafter referred to as "Solution B") and a solution containing bicarbonate ion ($HCO_3^-$) (hereinafter referred to as "Solution A", which are kept separately and mixed together on use (Patent Reference 1).

Patent Reference 1: JP-A-2005-28108;
Non-Patent Reference 1: Critical care/intensive care, Vol. 18, No. 1.2:3-4, 2006 (Japanese Journal);
Non-Patent Reference 2: Japanese Journal of Clinical Medicine, Vol. 62 (Supp.):397-402, 2004.

An example of the dialysate or substitution liquid commercially available comprises sodium ion ($Na^+$), 132-143 mEq/L; potassium ion (K+), 2.0-2.5 mEq/L; calcium ion ($Ca^{2+}$), 2.5-3.5 mEq/L; magnesium ion ($Mg^{2+}$), 1.0-1.5 mEq/L; chloride ion ($Cl^-$), 104-114.5 mEq/L; bicarbonate ion ($HCO_3^-$), 0-35.0 mEq/L; acetate ion ($CH_3COO^-$), 3.5-40 mEq/L; and glucose, 0-200 mg/dL.

For instance, said Sublood®-BS comprises a double chambered container having an upper chamber and a lower chamber separated with a separation wall, the upper and lower chambers containing respectively the following Solutions B and A:

Solution B comprising the following compounds in a volume of 1010 mL (pH, 3.8-3.9; osmotic pressure ratio, 0.9-1.0): sodium chloride (NaCl), 7.88 g; calcium chloride ($CaCl_2 \cdot 2H_2O$), 519.8 mg; magnesium chloride ($MgCl_2 \cdot 6H_2O$), 205.4 mg; sodium acetate ($CH_3COONa$), 82.8 mg; glucose ($C_6H_{12}O_6$), 2.02 g; and glacial acetic acid ($CH_3COOH$), 360.0 mg; and Solution A comprising the following compounds in a volume of 1010 mL (pH, 7.9-8.5; osmotic pressure ratio, 0.9-1.0): sodium chloride (NaCl), 4.460 g; potassium chloride (KCl), 0.30 g; and sodium bicarbonate (($NaHCO_3$), 5.940 g.

On the use, the separation wall is broken to communicate the upper and lower chambers and combine Solutions A and B together, and the resultant mixture is administered from the side of the lower chamber. The double chambered container as above is used for keeping separately such active components which are expected to be reacted in the coexistence of them as bicarbonate ion and calcium and/or magnesium ions.

Other examples of the drug solution comprising bicarbonate ion are peritoneal dialysate, bicarbonate Ringer's solution, high calorie transfusion, etc., and most of them also keep bicarbonate ion and calcium and/or magnesium ions separately by accommodating them in a double chambered container in order to avoid the reaction between them (cf. JP-A-11-197240, etc.).

DISCLOSURE OF INVENTION

Problem to be Solved

However, conventional dialysates or substitution liquids as above produce sometimes adverse effects in the acute blood purification therapy, because the electrolyte concentrations therein are adjusted to be suitable for application not to patients in need of acute blood purification but to chronic renal failure patients.

For instance, the potassium ion concentration in commercially available dialysates or substitution liquids is adjusted so low as 2.0-2.5 mEq/L for improvement of hyperkalemia. Therefore, the application of those dialystates or substitution liquids to the case in need of acute blood purification having a serum potassium ion level of less than 4.0 mEq/L before dialysis may produce removal of potassium ion and amelioration of acidosis resulting in rapid depression of serum potassium ion level to cause a risk of induction of arrhythmia and digitalis intoxication.

Also, commercially available dialysates or substitution liquids are formulated for chronic renal failure patients requiring amelioration of hyperphosphatemia and do not contain any phosphorous component. Because of this reason, their application to the case in need of acute blood purification having such a low phosphate ion level as 3.0 mg/dL or less before dialysis may produce a risk of developing hypophosphatemia, leading to depression of immunity and, in a severe case, unconsciousness.

In the acute blood purification therapy using commercially available dialysates or substitution liquids, it is thus needed to correct the electrolyte concentrations by supplementing potassium and/or phosphate ions through the blood circuit for prevention of hypokalemia or hypophosphatemia.

Further, an acetate was used as an alkalizing agent (i.e. blood buffer) for a dialysate in the past. Acetate ion is transferred through a dialysis membrane into blood and then metabolized to become bicarbonate ion. However, as the result of having a dialyzer made of larger area and higher performance, the loaded amount of acetate often exceeds the treatment capacity of a living body and causes the symptoms of acetate intolerance such as reduction in blood pressure, bad feeling, headache and nausea (Earnest D L et al.: Trans. Am. Soc. Artif. Intern. Organs 14:434-437, 1968). A bicarbonate is currently used as the alkalizing agent in place of an acetate, but a small amount of acetate is yet contained for stabilization of pH. Therefore, a dialysate or substitution liquid free of acetate ion is needed for avoiding the symptoms of acetate intolerance.

The problems as stated above may be considered to solve by making conventional dialysates or substitution liquids higher in potassium ion concentration, incorporated with phosphate ion and/or not using any compound producing acetate ion. However, dialysates or substitution liquids have a possibility of affording a delicate and significant influence on the physiological state or condition of a living body, and therefore it is hardly predictable if a desired effect would be actually obtained by said modifications. In addition, as well known, phosphate ion reacts with calcium and/or magnesium ions to form insoluble fine particles or precipitates like bicarbonate ion. Therefore, it is unlikely that incorporation of phosphate ion into dialysates or substitution liquids would give a stable solution.

In addition, as stated above, it is difficult to keep bicarbonate ion and calcium and/or magnesium ions stable in a drug solution containing sodium bicarbonate for a long time. Because of this reason, a solution containing bicarbonate ion and a solution containing calcium and/or magnesium ions are prepared separately and mixed together just before the administration to a patient. However, after mixing, bicarbonate ion is released as carbon dioxide gas from the mixed solution with lapse of time so that the pH value rises and, in case of it being over around 7.5, the formation of insoluble fine particles or precipitates may start. In the acute blood purification therapy, blood purification is performed especially in the coexistence of bicarbonate ion and calcium and/or magnesium ions over a long period of time, and therefore the formation of insoluble fine particles or participates such as calcium and/or magnesium carbonates causes a big problem.

Recently, there has been developed a drug solution of single type, in which bicarbonate ion and calcium and/or magnesium ions coexist (Japanese Patent No. 3003504). In this drug solution, citric acid or citrate ion is used as a pH adjuster, by which the pH is adjusted to pH 7.0-7.8 to prevent the formation of insoluble fine particles or precipitates and provide a stable electrolyte infusion.

As stated above, citric acid or citrate ion is used as a pH adjuster in the formulation of infusion, but care must be taken for exertion of only the desired pH adjusting effect without any adverse effect such as citrate intoxication or drop of calcium ion concentration caused by the chelating action of citrate ion. The symptoms of citrate intoxication include reduction in blood pressure, depression of cardiac function, abnormality on electrocardiogram (ECG), etc., and it is reported that the cause of them is the lowering of calcium ion concentration in blood due to citric acid (Modern Medical Laboratory, Vol. 19, No. 2, 1991). Especially in case of an infusion which is administered directly into a blood vessel, it is not rare that the dosage of the drug solution is over 1-2 L. Also, in the acute blood purification therapy, the volume of a drug solution for substitution may sometimes reach to so large as several tens liters. With increase of the dosage, the amount of citrate to be administered to a patient becomes larger, whereby the occurrence of citrate intoxication, the depression of blood calcium ion concentration due to the chelating action of citrate ion, etc. may take place causing a problem for safety.

Means to Solve Problem

As a result of the extensive study, it has now have been found that a drug solution for acute blood purification of good stability, which does not induce the development of hypokalemia or hypophosphatemia, can be provided by keeping the concentrations of potassium ion and phosphate ion within certain ranges. It has also been found that a drug solution for acute blood purification of good stability, which does not induce the symptoms of acetate intolerance, can be provided by avoiding the use of any acetate compound producing acetate ion in the drug solution. The drug solution as above comprises calcium and/or magnesium ions but the incorporation of phosphate ion therein does not give insoluble phosphate salt. Further, said drug solution comprises bicarbonate ion and calcium and/or magnesium ions, but the presence of phosphate ion prevents the formation of insoluble carbonate salt even after a long period of time affording such a high pH value as 7.5 or more. These technical effects are entirely of unexpected nature. The present invention is based on the above findings.

Accordingly, the present invention provides a stable drug solution, in which the formation of insoluble fine particles or precipitates is prevented for a long time, characterized in that the drug solution comprises phosphate ion in the coexistence of bicarbonate ion and calcium and/or magnesium ions. It also provides a stable drug solution for acute blood purification, in which the formation of insoluble fine particles or precipitates is prevented for a long time, characterized in that compared with conventional dialysates or substitution liquids, a concentration of potassium ions in the drug solution is higher, and phosphate ions are contained. In the drug solution as above, it is preferred to maintain the potassium ion concentration within a range of 3.5-5.0 mEq/L and the phosphate ion concentration within a range of 2.3-4.5 mg/dL. Maintenance of the potassium ion concentration within the above range is for prevention of the development of hypokalemia. Maintenance of the phosphate ion concentration within the above range is for prevention of the development of hypophosphatemia with keeping the stability of the drug solution. At least within the above range, a higher phosphate ion concentration may retain the stability of the drug solution for a long time. In addition, it is preferred for prevention of the development of acetate intolerance that the drug solution is free of acetate ion.

Since the drug solution of the present invention comprises bicarbonate ion and calcium and/or magnesium ions as the essential components, there remains a possibility that insoluble fine particles or precipitates may be formed by the reaction of these ions, despite the presence of phosphate ion. Therefore, it is preferred to keep an aqueous solution comprising bicarbonate ion and an aqueous solution comprising calcium and/or magnesium ions in separate containers and combine those solutions on use to make a mixture of them. Usually, bicarbonate ion is contained in Solution A to be accommodated in a lower chamber of a double chambered container, and calcium and/or magnesium ions are contained in Solution B to be accommodated in an upper chamber. Potassium ion and phosphate ion may be incorporated together or individually in either one or both of Solutions A and B.

Effect of Invention

The dialysate or substitution liquid for acute blood purification provided by the present invention do not cause hypokalemia or hypophosphatemia, and it is not needed to revise the electrolyte concentrations during the acute blood purification therapy. Also, in case of acetate ion being not contained, it may be used for patients of acetate intolerance with safety. Further, the bicarbonate ion-containing drug solution of mixing type on use provided by this invention is prevented from formation of insoluble fine particles or precipitates such as calcium carbonate or magnesium carbonate over a long time after mixing and therefore suitable for the use in the acute blood purification therapy over a long period of time.

BRIEF DESCRIPTION OF DRAWINGS

The FIGURE shows a double chambered container of double bag type provided with a separation wall which is breakable for communication between the chambers.

EXPLANATION OF NUMERAL SIGN

1: Double chambered container accommodating the drug solution of the present invention;
2: Separation wall breakable for communication;
3: Lower chamber (Chamber A; administration side):
3': Upper chamber (Chamber B);
4: Heat seal portion;
5: Opening gate as a port for administration of the drug solution provided with a stopper, for instance, made of rubber or the like;
6: Opening as a port for supplying the drug solution.

BEST MODE FOR CARRYING OUT INVENTION

In an embodiment of the present invention, there is provided a drug solution of mixing type on use, especially a dialysate or substitution liquid for acute blood purification of mixing type on use, which comprises Solution B comprising a phosphorous component, preferably phosphate ion or a phosphate. In a preferred embodiment, there is provided a drug solution of mixing type on use, especially a dialysate or substitution liquid for acute blood purification of mixing type on use, which comprises Solution A comprising at least sodium ion, bicarbonate ion and water and Solution B comprising at least sodium ion, chloride ion, phosphate ion and water.

In another embodiment of this invention, there is provided a drug solution of mixing type on use, especially a dialysate or substitution liquid of mixing type on use for acute blood purification, which comprises Solution A comprising sodium ion, potassium ion, chloride ion, bicarbonate ion and water and Solution B comprising sodium ion, potassium ion, calcium ion, magnesium ion, chloride ion, phosphate ion, glucose and water, those Solutions being combined together on use to give the drug solution.

In another embodiment of this invention, there is provided a drug solution of mixing type on use, especially a dialysate or substitution liquid of mixing type on use for acute blood purification, which comprises Solution A comprising sodium bicarbonate, potassium chloride, sodium chloride and water and Solution B comprising sodium chloride, potassium chloride, calcium chloride, magnesium chloride, sodium dihydrogen phosphate, glucose and water, those Solutions being combined together on use to give the drug solution.

In another embodiment of this invention, there is provided a drug solution of mixing type on use, especially a dialysate or substitution liquid of mixing type on use for acute blood purification, which comprises Solution A comprising sodium ion, potassium ion, chloride ion, bicarbonate ion, phosphate ion and water and Solution B comprising sodium ion, potassium ion, calcium ion, magnesium ion, chloride ion, glucose and water, those solutions being combined together to give the drug solution.

In another embodiment of this invention, there is provided a drug solution of mixing type on use, especially a dialysate or substitution liquid of mixing type on use for acute blood purification, which comprises Solution A comprising sodium bicarbonate, potassium chloride, sodium chloride, disodium hydrogen phosphate and water and Solution B comprising sodium chloride, potassium chloride, calcium chloride, magnesium chloride, glucose and water, those Solutions being combined together on use to give the drug solution.

In another embodiment of this invention, there is provided a drug solution of mixing type on use, especially a dialysate or substitution liquid of mixing type on use for acute blood purification, which comprises Solution A comprising sodium bicarbonate, potassium chloride, sodium chloride and water and Solution B comprising sodium chloride, calcium chloride, magnesium chloride, glucose and water, at least one of Solutions A and B comprising further a phosphate compound and those Solutions being combined together on use to give the drug solution.

In a further embodiment of the invention, there is provided a drug solution of mixing type on use, especially a dialysate or substitution liquid of mixing type on use for acute blood purification, which has the same composition as that of any one of the above embodiments, a mixed solution of Solutions A and B having a potassium ion concentration within a range of 3.5-5.0 mEq/L.

In a further embodiment of the invention, there is provided a drug solution of mixing type on use, especially a dialysate or substitution liquid of mixing type on use for acute blood purification, which has the same composition as that of any one of the above embodiments, a mixed solution of Solutions A and B having a monophosphate ion concentration within a range of 2.3-4.5 mg/dL as an inorganic phosphorous concentration.

In a further embodiment of the invention, there is provided a drug solution of mixing type on use, especially a dialysate or substitution liquid of mixing type on use for acute blood purification, which comprises Solution A comprising sodium chloride (NaCl) (4.640 g), potassium chloride (KCl) (0.298 g), sodium bicarbonate (NaHCO$_3$) (5.377 g) and water per 1000 mL and Solution B comprising sodium chloride (NaCl) (7.598 g), potassium chloride (KCl) (0.298 g), calcium chloride (CaCl$_2$.2H$_2$O) (0.368 g), magnesium chloride (MgCl$_2$. 6H$_2$O) (0.203 g), sodium dihydrogen phosphate (NaH$_2$PO$_4$.2H$_2$O) (0.403 g), glucose (C$_6$H$_{12}$O$_6$) (2.00 g) and water per 1000 mL, those Solutions being combined together to give the drug Isolution.

In a further embodiment of the invention, there is provided a drug solution of mixing type on use, especially a dialysate or substitution liquid of mixing type on use for acute blood purification, which comprises Solution A comprising sodium chloride (NaCl) (4.382 g), potassium chloride (KCl) (0.298 g), sodium bicarbonate (NaHCO$_3$) (5.377 g), disodium hydrogen phosphate (Na$_2$HPO$_4$.12H$_2$O) (0.925 g) and water per 1000 mL and Solution B comprising sodium chloride (NaCl) (7.706 g), potassium chloride (KCl) (0.298 g), calcium chloride (CaCl$_2$.2H$_2$O) (0.368 g), magnesium chloride (MgCl$_2$.6H$_2$O) (0.203 g), glucose (C$_6$H$_{12}$O$_6$) (2.00 g) and water per 1000 mL, those Solutions being combined together on use to give the drug solution.

In a preferred embodiment of the invention, there is provided a drug solution of mixing type on use, especially a dialysate or substitution liquid of mixing type on use for acute blood purification, which is capable of retaining the potassium ion concentration in plasma within a normal range without a significant variation of the inorganic phosphate ion (iP) concentration in plasma over 24 hours from the beginning of the acute blood purification therapy when a mixed solution of Liquids A and B is administered to a mammal (including human).

In a further embodiment of the invention, there is provided a drug solution of mixing type on use, especially a dialysate or substitution liquid of mixing type on use for acute blood purification, which is capable of not causing the development of acetate intolerance to a mammal (including human) of acetate intolerance when a mixed solution of Solutions A and B is administered to the mammal (including human).

In a preferred embodiment of the invention, there is provided a container accommodating a drug solution of mixing type on use, especially a dialysate or substitution liquid of mixing type on use for acute blood purification, which comprises an upper chamber and a lower chamber divided with a separation wall and a closed opening gate provided at the bottom of the lower chamber and accommodates Solution A comprising sodium ion, potassium ion, chloride ion and bicarbonate ion in the lower chamber and Solution B comprising sodium ion, potassium ion, calcium ion, magnesium ion, chloride ion and glucose in the upper chamber, at least one of Liquids A and B comprising additionally phosphate ion and the separation wall being broken on use to combine Solutions A and B together. Preferably, said separation wall is easily breakable.

In a further embodiment of the invention, there is provided the container as above, which is provided with a suspending means at the top of the upper chamber. An example of the suspending means is a hole for hanging.

In a still further embodiment of the invention, there is provided either one of the containers as above, wherein the separation wall is provided to make the capacities of the upper and lower chambers equal or nearly equal.

In a still further embodiment of the invention, there is provided any one of the containers as above, which is made of an elastic and transparent plastic material.

In a still further embodiment of the invention, there is provided any one of the containers as above, wherein Solution A is an aqueous solution comprising sodium bicarbonate, potassium chloride and sodium chloride and Solution B is an aqueous solution comprising sodium chloride, potassium chloride, calcium chloride, magnesium chloride and glucose, at least one of Solutions A and B comprising further a phosphate compound.

The container according to the invention may comprise two or more chambers for accommodating a drug solution. For instance, it may be a container comprising an upper chamber (Chamber B) and a lower chamber (Chamber A; administration side) divided with a separation wall which is breakable to communicate those chambers. The upper chamber is a chamber accommodating a solution as one of the constituents of the drug solution and being to be positioned at an upper side on administration of the drug solution. For instance, it is indicated by the numeral 3' in the FIGURE. The separation wall to be broken for communication may be constructed in any optional state or form, for instance, as a wall formed by separable melt-adhesion seal, a wall formed by fastening with a clip or a wall formed with an easily breakable material. From the viewpoint of simplicity in construction, preferred is a container having a separation wall formed as a weakly sealed portion by heat fusion to make readily separable. The separation wall of such container is readily broken by application of a pressure from the outside onto either one of the chambers so as to make the sealed portion separated, thereby the solutions in the chambers being mixed together aseptically.

The sealing may be made weakly by fusing two opposite films to make the fusion separable with ease. Such fusion may be prepared by a conventional procedure for preparation of a double chambered container such as a double bag. For instance, an adhesive resin may be applied to the surfaces of the films to be combined. Also, a fusible resin may be sandwiched between the films, followed by heat fusion. Further, the heating temperature for sealing may be set at a temperature somewhat lower than a perfect fusion temperature.

In the accompanying drawing, the FIGURE shows an example of a double chambered container of double bag type provided with a separation wall which is easily breakable. In the FIGURE, the numeral 1 indicates a double chambered container accommodating the drug solution of the invention, the numeral 2 indicates a separation wall which is easily breakable, the numeral 3 indicates a lower chamber (Chamber A; administration side), the numeral 3' indicates an upper chamber (Chamber B) and the numeral 4 indicates a heat fused part.

The container 1 is provided with an opening gate 5 as an administration port having a stopper made of rubber or the like on one edge and an opening 6 as a supply port on the other edge. In the FIGURE, the container 1 is divided into two chambers, i.e. the upper chamber and the lower chamber. However, the number of chambers is not limitative and also the container may be divided optionally to have three or more chambers, if desired. Further, no limitation is present on the shapes of the container and each chamber as well as the width and shape of the sealing portion for a separation wall. Two chambers are usually formed by dividing them with one sealing, but two or more sealing may be applied to form three or more chambers.

The double chambered container for accommodating a drug solution of mixing type on use according to the invention is usually prepared by the use of film sheets made of any synthetic resin as conventionally employed for preparation of containers for accommodating medicinal infusions. Examples of the film sheets are mono-layer films, laminated films, etc. made of low density polyethylene, ultra-low density polyethylene, high density polyethylene, polypropylene, ethylene-vinyl acetate copolymer, polyester, polyvinyl chloride, polybutadiene, polyimide, ethylene-methacrylate copolymer, ethylene-propylene elastomer, etc. The film sheets may be prepared by a per se conventional procedure such as blow molding, inflation molding, T-die molding, multi-layer molding or co-extrusion molding.

A double chambered container accommodating different solutions separately in different chambers divided with a separation wall which is breakable for communication can be prepared by a per se conventional procedure. Such conventional procedure will be briefly illustrated below.

A laminated film consisting of three layers, i.e. an inner layer of low density polyethylene (0.1 mm thick), a middle layer of ethylene-propylene elastomer (0.3 mm thick) and an outer layer of high density polyethylene (0.1 mm thick) is prepared by co-extrusion technique. Two sheets of the laminated film are cut in a designed size, and an opening gate 5 as an administration port is inserted between the two sheets in a manner communicating with the chamber for accommodating a drug solution. Then, the periphery 4 (except the portion corresponding to the opening 6 as a supply port) and the separation wall 2 are subjected to heat fusion.

Into the double chambered container as prepared above, a drug solution to be mixed on use may be filled in a per se conventional procedure. For instance, Solution A comprising sodium chloride (NaCl) (4.640 g), potassium chloride (KCl) (0.298 g) and sodium bicarbonate (NaHCO$_3$) (5.377 g) per 1000 mL is first filled in the chamber 3 through the opening gate 5, followed by closing said opening gate with a rubber stopper. Then, Solution B comprising sodium chloride (NaCl) (7.598 g), potassium chloride (KCl) (0.298 g), calcium chloride (CaCl$_2$.2H$_2$O) (0.368 g), magnesium chloride (MgCl$_2$.6H$_2$O) (0.203 g), sodium dihydrogen phosphate (NaH$_2$PO$_4$.2H$_2$O) (0.403 g), glucose (C$_6$H$_{12}$O$_6$) (2.00 g) per 1000 mL is filled in the chamber 3' through the opening 6, followed by sealing said opening by heat fusion. Finally, the resultant container filled in by the drug solution, i.e. Solutions A and B, is sterilized by steaming at 110° C. under pressure for 30 minutes according to the guidance of the Japanese Pharmacopoeia (JP) to obtain a final product.

Also, for instance, Solution A comprising sodium chloride (NaCl) (4.382 g), potassium chloride (KCl) (0.298 g), sodium bicarbonate (NaHCO$_3$) (5.377 g) and disodium hydrogen phosphate (Na$_2$HPO$_4$.12H$_2$O) (0.925 g) per 1000 mL is filled in the chamber 3 through the opening gate 5, followed by closing with a rubber stopper. Then, Solution B comprising sodium chloride (NaCl) (7.706 g), potassium chloride (KCl) (0.298 g), calcium chloride (CaCl$_2$.2H$_2$O) (0.368 g), magnesium chloride (MgCl$_2$.6H$_2$O) 0.203 g and glucose (C$_6$H$_{12}$O$_6$) 2.00 g) per 1000 mL is filled in the chamber 3' through the opening 6, followed by heat fusion adhesion. Finally, the resultant container filled in by the drug solution, i.e. Solutions A and B, is sterilized by steaming at 100° C. under pressure for 30 min according to the guidance of JP to obtain a final product.

After accommodation of the drug solution in the double chambered container shown in the FIGURE as above, heat sterilization is applied thereto as exemplified above. The heat sterilization may be performed by autoclaved sterilization, hot water spray sterilization, hot water shower sterilization, hot water soaking sterilization or the like. The sterilization condition may depend on the sterilization procedure as applied and is generally heated at a temperature of 100-130° C., preferably 105-120° C., for 15-30 minutes.

The thus obtained double chambered container in which the drug solution is aseptically accommodated is preferably stored in an outer packaging container made of a gas impermeable material in order to prevent the contact with air. As the gas impermeable material suitable for this purpose, there are known various kinds of materials such as ethylene-vinyl alcohol copolymer, from which any one may be optionally chosen and used. Further, in order to keep the atmosphere in the outer packaging container free of oxygen, the double chambered container may be stored in the presence of a deoxidant and/or under an atmosphere of nitrogen gas or carbon dioxide gas. Furthermore, an oxygen detector or the like may be provided in the outer packaging container for the purpose of detecting a pinhole.

In the present specification, the language "formation of insoluble fine particles or precipitates is prevented for a long time" is intended to mean that the formation of insoluble fine particles or precipitates is prevented at least over 27 hours after the final drug solution such as a mixed solution of Solutions A and B is prepared or inhibited even after the pH of the mixed solution rises to 7.5 or more.

The term "drug solution of mixing type on use" is intended to mean a drug solution consisting comprising Solutions A and B and being used (i.e. administered) after combination of those Solutions.

The term "drug solution for acute blood purification" means a dialysate or substitution liquid to be used in the acute blood purification therapy (i.e. the blood purification therapy in critical care). The term "acute blood purification therapy" is used in the same meaning as commonly used in the related art field. The term "substitution liquid" is sometimes referred to as "rehydration", "replacement fluid" or the like. In addition, the term "drug solution of mixing type on use for acute blood purification" means a dialysate or substitution liquid to be used in the acute blood purification therapy, amongst drug solutions to be mixed on use.

The term "Solution A" means a drug solution comprising at least sodium ion, bicarbonate ion and water. Preferably, it comprises sodium ion, potassium ion, chloride ion, bicarbonate ion and water.

The term "Solution B" means a drug solution comprising at least calcium ion and/or magnesium ion and water. Preferably, it comprises sodium ion, calcium ion, magnesium ion, chloride ion, glucose and water. Still, the components in Solutions A and B other than water may be formulated in a solid form and dissolved in water on use to make a solution form.

As stated above, the drug solution of the invention is characterized in comprising potassium ion and phosphate ion. The source of potassium ion may be chosen from compounds capable of giving potassium ion in an aqueous solution such as inorganic potassium salts (e.g. potassium chloride) and organic potassium salts (e.g. potassium lactate, potassium gluconate). The source of phosphate ion may be chosen from compounds capable of giving phosphate ion in an aqueous solution such as phosphoric acid, sodium phosphate, sodium dihydrogen phosphate and disodium hydrogen phosphate. Further, compounds comprising potassium and phosphate ions such as potassium phosphate, dihydrogen potassium phosphate and dipotassium hydrogen phosphate may be used as the source of potassium and phosphate ions.

The concentration of potassium ion in the drug solution is usually 3.5-5.0 mEq/L, preferably 3.5-4.5 mEq/L, and the concentration of monophosphate ion as an inorganic phosphorous concentration is usually 2.3-4.5 mg/dL, preferably 2.5-4.0 mg/dL (especially 3.0 mg/dL or more). As stated above, the drug solution of the invention usually consists of two solutions, i.e. Solution A and Solution B, and the concentrations of potassium ion and/or phosphate ion in each of said two solutions may be so adjusted as giving the concentrations as stated above in the drug solution obtained by combination of said two Solutions.

Practical embodiments of the present invention will be hereinafter explained more in details by way of Examples, but it is to be understood that those Examples are not intended to make any limitation onto the technical scope of the present invention. The apparatuses and reagents used in those Examples are as follows:

Dialyzer (APS-08MD; membrane area, 0.7 m$^2$; Lot No. 01Z182082; Asahi Kasei Medical Co., Ltd.)
Blood circuit for sustained filtration (JCH-26S; Lot No. 012942; UBE JUNKEN MEDICAL Co., LTD.)
Blood purification device (JUN-505; Serial No. UA034; UBE JUNKEN MEDICAL Co., LTD.)
Solution sending pump (Masterflex L/S; Cole-Parmer)
Solution sending pump (Watson Marlow 505Di; Serial No. B00005470, B00005471; WATSON-MARLOW)
Syringe pump (Terufusion Syringe pump STC-521; Serial No. 8063084; Termo)
Polygraph system (RM-7000; NIHON KOHDEN)
 Amplifier for blood pressure measurement AP-641G
 Blood pressure transducer (Lifekit; DX-312; Lot No. 107087)
 Amplifier for bioelectricity AB-621G
 Input box for bioelectricityJB-640G
 Amplifier for copula AA-601H
 Breath/pulse wave copula AR-650H
 Temperature measurement unit AW-601H
 Temperature copula AW-650H
Inhalation anesthesia apparatus
Universal blood gas analysis apparatus (i-STAT analyzer 300F; Fuso Pharmaceutical Industries, Ltd.)
Universal blood gas analysis apparatus (i-STAT cartridge EG7+; Lot No. M02164B; Fuso Pharmaceutical Industries, Ltd.)
Dry-type Clinical Chemistry Analyzer (FUJI DRI-CHEM 3030; FUJIFILM Medical Co., Ltd.)
Dry-type Clinical Chemistry Analyzer (FUJI DRI-CHEM 800; FUJIFILM Medical Co., Ltd.)
High speed micro centrifuge (MX-150; TOMY SEIKO CO., LTD.)
Substitution liquid for filtration type artificial kidneys (Sublood-BS; Lot No. 02D11A; Fuso Pharmaceutical Industries, Ltd.)
Lactate Ringer's solution (Lactate Ringer's solution "FUSO"; Fuso Pharmaceutical Industries, Ltd.)
Isoflurane
Sodium taurocholate (Wako Pure Chemical Industries, Ltd.)
Benzylpenicillin potassium (PENICILLIN G POTASSIUM 500,000 UNITS FOR INJECTION; Lot No. 7QC02P; MEIJI SEIKA KAISHA, LTD.)
Heparin sodium (Heparin sodium injection; Lot No. 02G08A; Fuso Pharmaceutical Industries, Ltd.)

EXAMPLES

<Preparation of Acute Pancreatitis Model Animal>

In a large animal facility of Fuso Pharmaceutical Industries, Ltd. (temperature, 23±5° C.; humidity, 50±20% RH; ventilation, 15-20 times/hr; lighting, 12 hours (7:00-19:00)), 21 ma beagle dogs (each weighing around 10 kg, Nosan Corporation) were accommodated each in a stainless breeding case and bred with a solid feed (CREA Dog Diet CD-5M™, CLEA Japan, Inc.) in an amount of about 300 g/day. Drinking water used was tap water, and the animals could be accessed ad libitum during the test.

Under isoflurane inhalation anesthesia, the beagle dogs were each fixed in the back position, and then the common bile duct was exposed through an abdominal incision and the incision was closed by a clamp. The duodenum was incised, and a tube made of polyethylene (PE50, Becton, Dickinson and Company) was inserted from the minor duodenal papilla into the accessory pancreatic duct. Then, 3% sodium taurocholate physiological saline was injected retrogradely at 1.0 mL/kg/5 min to induce acute pancreatitis.

During the preparation of the model and after the surgery, an appropriate infusion was administered in an appropriate amount.

After the surgery, a benzylpenicillin potassium injection (0.5 million U/animal) was given intramuscularly once a day for two days to prevent infection, whereby acute pancreatitis model animals were prepared.

Example 1

(i) Preparation of Solution B, Followed by Filling in and Sealing of Upper Chamber The components in Table 1 are weighed, and glucose, sodium chloride, potassium chloride, magnesium chloride, calcium chloride and sodium dihydrogen phosphate are added to and dissolved in water for injection (Japanese Pharmacopoeia (JP)), followed by filtration. To the filtrate, water for injection is added to make a designed volume. The thus obtained solution is subjected to sterilized filtration by the use of a fine filter, and the filtrate is filled in the upper chamber of a double bag made of colorless plastic (1000 mL/1000 mL). The opening, through which the filtrate has been introduced, is fused by heating to seal. The solution prepared with the prescription of Table 1 and accommodated in the upper chamber is called "upper chamber solution of Example 1" (Solution B).

TABLE 1

| | Prescription | Amount (per 1000 mL) |
|---|---|---|
| Upper chamber solution of Example 1 (Solution B) | Sodium chloride (NaCl), JP | 7.598 g |
| | Potassium chloride (KCl), JP | 0.298 g |
| | Calcium chloride (CaCl$_2$•2H$_2$O), JP | 0.368 g |
| | Magnesium chloride (MgCl$_2$•6H$_2$O) JSPI | 0.203 g |
| | Sodium dihydrogen phosphate (NaH$_2$PO$_4$•2H$_2$O) JSFA | 0.403 g |

TABLE 1-continued

| Prescription | Amount (per 1000 mL) |
| --- | --- |
| Glucose ($C_6H_{12}O_6$), JP | 2.000 g |
| Water for injection, JP | q.s. |

(ii) Preparation of Solution A, Followed by Filing in and Sealing of Lower Chamber The components in Table 2 are weighed, sodium chloride, potassium chloride and sodium bicarbonate are added to and dissolved in water for injection (JP), followed by filtration. To the filtrate, water for injection is added to make a designed volume. The thus obtained solution is subjected to sterilized filtration by the use of a fine filter, and the filtrate is filled in the lower chamber of the double bag (1000 mL/1000 mL) accommodating Solution B in the upper chamber as in (i). The opening gate, through which Solution A has been introduced, is closed with a rubber stopper, and the head of the rubber stopper is applied with a sealing cap, followed by fusion. The solution prepared with the prescription of Table 2 is called "lower chamber solution of Example 1" (Solution A).

TABLE 2

| | Prescription | Amount (per 1000 mL) |
| --- | --- | --- |
| Lower chamber solution of Example 1 (Solution A) | Sodium chloride (NaCl), JP | 4.640 g |
| | Potassium chloride (KCl), JP | 0.298 g |
| | Sodium bicarbonate ($NaHCO_3$), JP | 5.377 g |
| | Water for injection, JP | q.s. |

Example 2

(i) Preparation of Solution B, Followed by Filing in and Sealing of Upper Chamber The components in Table 3 are weighed, glucose, sodium chloride, magnesium chloride, and calcium chloride are added to and dissolved in water for injection (JP), and hydrochloric acid is added thereto, followed by filtration. To the filtrate, water for injection is added to make a designed volume. The thus obtained solution is subjected to sterilized filtration by the use of a fine filter, and the filtrate is filled in the upper chamber of a double bag made of colorless plastic (1000 mL/1000 mL). The opening, through which the filtrate has been introduced, is fused by heating to seal. The solution prepared with the prescription of Table 3 and accommodated in the upper chamber is called "upper chamber solution of Example 2" (Solution B).

TABLE 3

| | Prescription | Amount (per 1000 mL) |
| --- | --- | --- |
| Upper chamber solution of Example 2 | Sodium chloride (NaCl), JP | 7.706 g |
| | Potassium chloride (KCl), JP | 0.298 g |
| | Calcium chloride ($CaCl_2 \cdot 2H_2O$), JP | 0.368 g |

TABLE 3-continued

| | Prescription | Amount (per 1000 mL) |
| --- | --- | --- |
| (Solution B) | Magnesium chloride ($MgCl_2 \cdot 6H_2O$) JSPI | 0.203 g |
| | Glucose ($C_6H_{12}O_6$), JP | 2.000 g |
| | Hydrochloric acid (HCl), JP | q.s. |
| | Water for Injection, JP | q.s. |

(ii) Preparation of Solution A, Followed by Filing in and Sealing of Lower Chamber The components in Table 4 are weighed, and sodium chloride, potassium chloride, disodium hydrogen phosphate and sodium bicarbonate are added to and dissolved in water for injection (JP), followed by filtration. To the filtrate, water for injection is added to make a designed volume. The thus obtained solution is subjected to sterilized filtration by the use of a fine filter, and the filtrate is filled in the lower chamber of the double bag (1000 mL/1000 mL) accommodating Solution B in the upper chamber as in (i). The opening gate, through which Solution A has been introduced, is closed with a rubber stopper, and the head of the rubber stopper is applied with a sealing cap, followed by fusion. The solution prepared with the prescription of Table 4 is called "lower chamber liquid of Example 2" (Solution A).

TABLE 4

| | Prescription | Amount (per 1000 mL) |
| --- | --- | --- |
| Lower chamber solution of Example 2 (Solution A) | Sodium chloride (NaCl), JP | 4.382 g |
| | Potassium chloride (KCl), JP | 0.298 g |
| | Sodium bicarbonate ($NaHCO_3$), JP | 5.377 g |
| | Disodium hydrogen phosphate ($Na_2HPO_4 \cdot 12H_2O$) (JSFA) | 0.925 g |
| | Water for injection, JP | q.s. |

Comparative Example (i) Preparation of Solution B, Followed by Filling in and Sealing of Upper Chamber The components in Table 5 are weighed, and sodium chloride, calcium chloride, magnesium chloride, sodium acetate, glucose and glacial acetic acid are added to and dissolved in water for injection (JP) followed by filtration. To the filtrate, water for injection is added to make a total volume of 1010 mL. The thus obtained solution is subjected to sterilized filtration by the use of a fine filter, and the filtrate is filled in the upper chamber of a double bag made of colorless plastic (1000 mL/1000 mL). The opening, through which the filtrate has been introduced, is fused by heating to seal. The solution prepared with the prescription of Table 5 and accommodated in the upper chamber is called "upper chamber solution of Comparative Example" (Solution B). The upper chamber solution of Comparative Example has the same composition as Solution B of "Sublood®-BS" (Fuso Pharmaceutical Industries, Inc.).

TABLE 5

| | Prescription | Amount (per 1000 mL) |
|---|---|---|
| Upper chamber solution of Comparative Example (Solution B) | Sodium chloride (NaCl), JP | 7.88 g |
| | Calcium chloride (CaCl$_2$•2H$_2$O), JP | 0.5198 g |
| | Magnesium chloride (MgCl$_2$•6H$_2$O), JSPI | 0.2054 g |
| | Sodium acetate (CH$_3$COONa), JSPI | 0.0828 g |
| | Glucose (C$_6$H$_{12}$O$_6$), JP | 2.02 g |
| | Glacial acetic acid, JP | 0.3600 g |
| | Water for injection, JP | q.s. |

(ii) Preparation of Solution A, Followed by Filling in and Sealing of Lower Chamber The components in Table 6 are weighed, and sodium chloride, potassium chloride and sodium bicarbonate are added to and dissolved in water for injection (JP), followed by filtration. To the filtrate, water for injection is added to make a designed volume. The thus obtained solution A is subjected to sterilized filtration by the use of a fine filter, and the filtrate is filled in the lower chamber of the double bag (1000 mL/1000 mL) accommodating Solution B in the upper chamber as in (i). The opening gate, through which Solution A has been introduced, is closed with a rubber stopper, and the head of the rubber stopper is applied with a sealing cap, followed by fusion. The solution prepared with the prescription of Table 6 is called "lower chamber solution of Comparative Example" (Solution A). The lower chamber solution of Comparative Example has the same composition as Solution A of "Sublood®-BS".

TABLE 6

| | Prescription | Amount (per 1000 mL) |
|---|---|---|
| Lower chamber solution of Comparative Example (Solution A) | Sodium chloride (NaCl), JP | 4.460 g |
| | Potassium chloride (KCl), JP | 0.300 g |
| | Sodium bicarbonate (NaHCO$_3$), JP | 5.940 g |
| | Water for Injection, JP | q.s. |

<Qualitative Test>

The sugar and electrolyte concentrations (theoretical value) of a mixed solution of the upper chamber solution of Example 1 (Solution B) and the lower chamber solution of Example 1 (Solution A), a mixed solution of the upper chamber solution of Example 2 (Solution B) and the lower chamber solution of Example 2 (Solution A) and a mixed solution of the upper chamber solution of Comparative Example (Solution B) and the lower chamber solution of Comparative Example (Solution A) are shown in Table 7.

<CHDF Test>

(Method 1)

Beagle dog acute pancreatitis models (3 animals) were weighed 2 days after the induction of pancreatitis, and inhalation anesthesia with isoflurane were applied to them. A cannula connected to a blood pressure transducer was inserted into the right femoral artery and a rectal temperature probe was inserted into the rectum for monitoring the blood pressure and the body temperature, respectively. Measurement of the electrocardiogram (ECG) was done in Lead II. An arteriovenous shunt (detachable at center) provided with a blood collecting port from the left femoral artery to the right femoral vein was prepared. To inhibit clotting, an appropriate amount of heparin sodium injection (heparin) was administered from the blood collecting site of the arteriovenous shunt, and the injection was continued into a blood circuit thereafter. Five minutes after the administration of heparin, the blood access was connected with a blood circuit (JCH-26S, JUNKEN MEDICAL Co., LTD.) and a dialyzer (APS-08MD, Asahi Kasei Medical CO., LTD.).

(Method 2)

After Method 1 above, CHDF was done over 24 hours under the following conditions: blood flow rate, 20 mL/min; dialysate (Mixed solution of Example 1) flow rate, 1200 mL/hr; substitution liquid (Mixed solution of Example 1) flow rate, 300 mL/hr; filtrate (Mixed solution of Example 1) flow rate, 1500 mL/hr; and no water removal. 0, 3, 6, 9, 12, 15, 18, 21 and 24 hours after the beginning of CHDF, heparinized blood (1.5 mL) was collected from the blood collecting port (outlet venous blood). For the collected heparinized blood, various instrumental analyses were performed.

In an analogous manner, CHDF was done using a mixed solution of Comparative Example as the dialysate and the substitution liquid, and various instrumental analyses were performed.

Test items: pH, PCO$_2$ (mmHg), PO$_2$ (mmHg), HCO$_3^-$ (mmol/L), tCO$_2$ (mmol/L), sO$_2$ (%), BE (mmol/L), Hct (%), Hb (g/dL), Na$^+$ (mEq/L), K$^+$ (mEq/L), Cl$^-$ (mEq/L), Ca$^{2+}$ (mEq/L), Mg$^{2+}$ (mEq/L), Lac (mEq/L), Ca (mg/dL), Mg (mg/dL), iP (mg/dL), GPT (U/L), LDH (U/L), AMY (U/L), BUN (mg/dL), ALB (g/dL), GLU (mg/dL). The results are shown in Table 8 wherein an average obtained from three beagle dogs is given.

TABLE 7

| Mixed solution | Volume (mL) | Na$^+$ mEq/L | K$^+$ mEq/L | Ca$^{2+}$ mEq/L | Mg$^{2+}$ mEq/L | Cl$^-$ mEq/L | HCO$_3^-$ mEq/L | glucose mg/dL | P mg/dL | CH3COO$^-$ mEq/L |
|---|---|---|---|---|---|---|---|---|---|---|
| Ex. 1 | 1000 | 138.0 | 4.0 | 2.5 | 1.0 | 112.2 | 32.0 | 100.0 | 4.0 | — |
| Ex. 2 | 1000 | 138.0 | 4.0 | 2.5 | 1.0 | 111.0 | 32.0 | 100.0 | 4.0 | — |
| Com. Ex. | 1010 | 140.0 | 2.0 | 3.5 | 1.0 | 111.0 | 35.0 | 100.0 | — | 3.5 |

TABLE 8

| 3% TAU CHDF | | Before abdominal incision | 1 Day after surgeon | Time after beginning of CHDF (hr) | | | |
|---|---|---|---|---|---|---|---|
| | | | | 0 | 3 | 6 | 9 |
| pH | Com. Ex. | 7.366 | 7.383 | 7.437 | 7.422 | 7.446 | 7.452 |
| | Ex. 1 | 7.327 | 7.381 | 7.384 | 7.407 | 7.429 | 7.402 |
| $PCO_2$ (mmHg) | Com. Ex. | 34.9 | 36.9 | 27.4 | 34.6 | 33.7 | 32.9 |
| | Ex. 1 | 42.3 | 40.0 | 36.0 | 35.4 | 37.3 | 39.6 |
| $HCO_3^-$ (mmol/L) | Com. Ex. | 20.0 | 22.1 | 18.7 | 22.8 | 23.4 | 23.2 |
| | Ex. 1 | 22.3 | 24.0 | 21.7 | 22.5 | 24.9 | 24.9 |
| $tCO_2$ (mmol/L) | Com. Ex. | 21.1 | 23.2 | 19.5 | 23.8 | 24.4 | 24.2 |
| | Ex. 1 | 23.6 | 25.2 | 22.8 | 23.5 | 26.0 | 26.1 |
| Hct (%) | Com. Ex. | 46 | 46 | 34 | 33 | 31 | 31 |
| | Ex. 1 | 49 | 48 | 36 | 32 | 29 | 28 |
| Hb (g/dL) | Com. Ex. | 15.0 | 15.0 | 11.4 | 11.1 | 10.4 | 10.3 |
| | Ex. 1 | 16.1 | 15.4 | 11.9 | 10.5 | 9.7 | 9.6 |
| Na+ (mmol/L) | Com. Ex. | 149.7 | 146.9 | 144.0 | 141.8 | 140.7 | 139.7 |
| | Ex. 1 | 145.8 | 143.3 | 143.5 | 139.8 | 138.3 | 137.3 |
| $K^+$ (mmol/L) | Com. Ex. | 3.96 | 3.96 | 3.63 | 3.78 | 3.67 | 3.44 |
| | Ex. 1 | 4.17 | 3.55 | 3.70 | 3.95 | 3.79 | 3.62 |
| $Cl^-$ (mmol/L) | Com. Ex. | 115.2 | 110.6 | 114.4 | 109.9 | 109.4 | 109.1 |
| | Ex. 1 | 111.5 | 110.2 | 112.3 | 109.3 | 108.3 | 108.5 |
| Ca2+ (mmol/L) | Com. Ex. | 1.15 | 1.16 | 1.20 | 1.21 | 1.21 | 1.17 |
| | Ex. 1 | 1.24 | 1.23 | 1.24 | 1.16 | 1.14 | 1.14 |
| Mg2+ (mmol/L) | Com. Ex. | 0.35 | 0.46 | 0.45 | 0.42 | 0.42 | 0.41 |
| | Ex. 1 | 0.44 | 0.47 | 0.46 | 0.43 | 0.42 | 0.40 |
| Lac (mmol/L) | Com. Ex. | 2.5 | 1.6 | 1.5 | 0.9 | 0.6 | 0.7 |
| | Ex. 1 | 2.7 | 2.1 | 1.3 | 0.8 | 0.7 | 0.6 |
| Ca (mg/dL) | Com. Ex. | 9.8 | 9.7 | 9.1 | 9.2 | 9.0 | 8.7 |
| | Ex. 1 | 10.7 | 10.2 | 9.9 | 8.6 | 8.4 | 8.3 |
| Mg (mg/dL) | Com. Ex. | 1.5 | 1.7 | 1.5 | 1.5 | 1.5 | 1.5 |
| | Ex. 1 | 1.7 | 1.8 | 1.7 | 1.7 | 1.6 | 1.5 |
| IP (mg/dL) | Com. Ex. | 3.8 | 3.6 | 3.8 | 5.1 | 4.7 | 4.4 |
| | Ex. 1 | 5.0 | 3.9 | 5.4 | 5.9 | 5.4 | 5.3 |
| AMYL (U/L) | Com. Ex. | 885 | 7173 | 5698 | 3733 | 2955 | 2415 |
| | Ex. 1 | 1175 | 10783 | 9591 | 4808 | 3793 | 3563 |
| ALB (g/dL) | Com. Ex. | 3.1 | 3.3 | 2.5 | 2.4 | 2.2 | 2.1 |
| | Ex. 1 | 3.0 | 3.0 | 2.4 | 2.2 | 2.0 | 1.9 |
| GLU (mg/dL) | Com. Ex. | 90 | 102 | 120 | 124 | 127 | 131 |
| | Ex. 1 | 96 | 117 | 146 | 156 | 150 | 145 |

| 3% TAU CHDF | | Time after beginning of CHDF (hr) | | | | |
|---|---|---|---|---|---|---|
| | | 12 | 15 | 18 | 21 | 24 |
| pH | Com. Ex. | 7.446 | 7.431 | 7.431 | 7.437 | 7.428 |
| | Ex. 1 | 7.411 | 7.394 | 7.406 | 7.419 | 7.422 |
| $PCO_2$ (mmHg) | Com. Ex. | 33.6 | 35.3 | 34.1 | 32.4 | 34.6 |
| | Ex. 1 | 39.6 | 40.4 | 39.4 | 38.4 | 38.7 |
| $HCO_3^-$ (mmol/L) | Com. Ex. | 23.4 | 23.7 | 22.8 | 22.0 | 23.0 |
| | Ex. 1 | 25.4 | 24.9 | 24.9 | 25.1 | 25.4 |
| $tCO_2$ (mmol/L) | Com. Ex. | 24.4 | 24.8 | 23.9 | 23.0 | 24.1 |
| | Ex. 1 | 26.6 | 26.1 | 26.2 | 26.2 | 26.6 |
| Hct (%) | Com. Ex. | 30 | 30 | 30 | 30 | 29 |
| | Ex. 1 | 24 | 28 | 27 | 26 | 26 |

TABLE 8-continued

| | | | | | | |
|---|---|---|---|---|---|---|
| Hb (g/dL) | Com. Ex. | 9.9 | 10.1 | 10.1 | 10.1 | 9.8 |
| | Ex. 1 | 8.0 | 9.3 | 8.8 | 8.6 | 8.7 |
| Na+ (mmol/L) | Com. Ex. | 140.2 | 139.2 | 138.1 | 138.3 | 137.8 |
| | Ex. 1 | 136.7 | 136.7 | 136.6 | 134.9 | 135.0 |
| K+ (mmol/L) | Com. Ex. | 3.36 | 3.17 | 3.22 | 3.14 | 3.08 |
| | Ex. 1 | 3.63 | 3.65 | 3.58 | 3.54 | 3.43 |
| Cl− (mmol/L) | Com. Ex. | 108.6 | 108.7 | 109.0 | 108.6 | 108.7 |
| | Ex. 1 | 108.4 | 107.8 | 107.9 | 107.7 | 107.5 |
| Ca2+ (mmol/L) | Com. Ex. | 1.16 | 1.13 | 1.12 | 1.14 | 1.15 |
| | Ex. 1 | 1.15 | 1.14 | 1.13 | 1.13 | 1.12 |
| Mg2+ (mmol/L) | Com. Ex. | 0.40 | 0.38 | 0.38 | 0.38 | 0.39 |
| | Ex. 1 | 0.40 | 0.39 | 0.39 | 0.39 | 0.38 |
| Lac (mmol/L) | Com. Ex. | 0.6 | 0.6 | 0.6 | 0.8 | 0.6 |
| | Ex. 1 | 0.6 | 0.7 | 0.8 | 0.9 | 0.9 |
| Ca (mg/dL) | Com. Ex. | 8.4 | 8.3 | 8.2 | 8.1 | 8.0 |
| | Ex. 1 | 8.3 | 8.3 | 8.3 | 8.2 | 8.1 |
| Mg (mg/dL) | Com. Ex. | 1.4 | 1.3 | 1.3 | 1.3 | 1.3 |
| | Ex. 1 | 1.5 | 1.5 | 1.5 | 1.4 | 1.4 |
| IP (mg/dL) | Com. Ex. | 4.3 | 4.0 | 3.9 | 3.5 | 3.2 |
| | Ex. 1 | 5.0 | 4.9 | 4.7 | 4.5 | 4.5 |
| AMYL (U/L) | Com. Ex. | 2118 | 1942 | 1790 | 1717 | 1646 |
| | Ex. 1 | 3159 | 2799 | 2415 | 2089 | 1847 |
| ALB (g/dL) | Com. Ex. | 2.0 | 1.9 | 1.8 | 1.7 | 1.7 |
| | Ex. 1 | 1.8 | 1.8 | 1.7 | 1.6 | 1.5 |
| GLU (mg/dL) | Com. Ex. | 130 | 129 | 130 | 133 | 126 |
| | Ex. 1 | 142 | 141 | 140 | 142 | 137 |

(Results)

Reduction of potassium concentration after the beginning of CHDF with the mixed solution of Example 1 was slower than that with the mixed solution of Comparative Example, suggesting less induction of hypokalemia. Also, reduction of inorganic phosphorus (iP) concentration after the beginning of CHDF with the mixed solution of Example 1 was likewise slower than that with the mixed solution of Comparative Example, suggesting less induction of hypophosphatemia. No significant difference can be seen for other values measured. The above results thus suggest that the substitution liquid for acute blood purification according to the present invention may sufficiently inhibit the development of hypokalemia and hypophosphatemia.

<Stability Test>

Measurement of the pH and properties (color and clearness) of a drug solution for acute blood purification in the open system was done with variation of the concentration of disodium hydrogen phosphate.

(1. Test Solutions)

1-1. Sodium chloride (77.0625 g), potassium chloride (2.9804 g), calcium chloride dihydrate (3.6827 g), magnesium chloride hexahydrate (2.0315 g), glucose (20.0015 g) and 1 mol/L hydrochloric acid (2 mL) were obtained, and water was added thereto to make a volume of 2 L (5 fold conc. Stock Solution B).

1-2. Sodium chloride (43.8236 g), potassium chloride (2.9797 g) and sodium bicarbonate (53.7711 g) were obtained, and water was added thereto to make a volume of 2 L (5 fold conc. Stock Solution A).

1-3. Disodium hydrogen phosphate 12 hydrate (3.5804 g) was obtained, and water was added thereto to make a volume of 100 mL (disodium hydrogen phosphate solution)

1-4. Disodium hydrogen phosphate 12 hydrate (0.1153 g) was obtained, and 5 fold conc. Stock Solution A (100 mL) and water were added thereto to make a volume of 500 mL, followed by bubbling with carbon dioxide gas to make pH of about 7.5 (Solution A-1). Besides, water was added to 5 fold conc. Stock Solution B (100 mL) to make a volume of 500 mL (Solution B-1). Solution A-1 (500 ml) and Solution B-1 (500 ml) were mixed gently (P 1 mg/dL), followed by bubbling with carbon dioxide gas to make pH of about 7.25.

1-5. Disodium hydrogen phosphate 12 hydrate (0.2312 g) was obtained, and 5 fold conc. Stock Solution A (100 mL) and water were added thereto to make a volume of 500 mL, followed by bubbling with carbon dioxide gas to make pH of about 7.5 (Solution A-1). Besides, water was added to 5 fold conc. Stock Solution B (100 mL) to make a volume of 500 mL (Solution B-1). Each 500 mL of Solution A-1 and Solution B-1 were mixed gently (P 1 mg/dL), followed by bubbling with carbon dioxide gas to make pH of about 7.25.

1-6. Disodium hydrogen phosphate solution (0, 1, 2.5 or 5 mL) was obtained, and 5 fold conc. Stock Solution A (100 mL) and water were added thereto to make a volume of 500 mL, followed by bubbling with carbon dioxide gas to make pH of about 7.5 (Solutions A-2~A-5). Besides, water was added 5 fold conc. Stock Solution B (100 mL) to make a volume of 500 mL (Solution B-2). Solution A-2

(500 ml) and Solution B-2 (500 ml) were mixed gently (P 1 mg/dL), followed by bubbling with carbon dioxide gas to make pH of about 7.25. In an analogous manner, test solutions were prepared with Solutions A-3-A-5. (The phosphate ion concentrations are 0, 0.1, 0.25 or 0.5 mEq/L.)

(2. Date of Test)

Jul. 9 to 12, 2007 (monophosphate ion: 1 mg/dL and 2 mg/dL, as an inorganic phosphorous concentration)

Jul. 9 to 13, 2007 (monophosphate ion: 0, 0.1, 0.25 and 0.5 mEq/L)

(3. Test Method)

3-1. Each test solution was poured gently into a 1 L volume plastic bottle, followed by gentle stirring with a rotary bob (9 mm).

3-2. pH and property (clearness) were measured.

(4. Test Results)

4-1. monophosphate ion: 1 mg/dL (0.32 mEq/L) and 2 mg/dL (0.65 mEq/L)

TABLE 9

|  | 1 mg/dL (0.32 mEq/L) | | 2 mg/dL (0.65 mEq/L) | |
| --- | --- | --- | --- | --- |
|  | pH | Precipitate | pH | Precipitate |
| Beginning | 7.27 | — | 7.26 | — |
| 2 hrs | 7.33 | — | 7.29 | — |
| 17 hrs | 8.18 | — | 8.07 | — |
| 18 hrs | 8.23 | — | 8.12 | — |
| 20 hrs | 8.29 | — | 8.19 | — |
| 24 hrs | 8.41 | — | 8.32 | — |
| 42 hrs | 8.69 | — | 8.67 | — |
| 48 hrs | 8.73 | — | 8.70 | — |
| 67 hrs | 8.87 | — | 8.86 | — |
| 72 hrs | 8.88 | — | 8.89 | — |

4-2. Phosphate ion: 0, 0.1, 0.25 and 0.5 mEq/L

TABLE 10

|  | 0 mEq/L | | 0.1 mEq/L | | 0.25 mEq/L | | 0.5 mEq/L | |
| --- | --- | --- | --- | --- | --- | --- | --- | --- |
|  | pH | Precipitate | pH | Precipitate | pH | Precipitate | pH | Precipitate |
| Beginning | 7.26 | — | 7.27 | — | 7.23 | — | 7.27 | — |
| 2 hrs | 7.48 | — | 7.44 | — | 7.45 | — | 7.45 | — |
| 4 hrs | 7.60 | — | 7.52 | — | 7.53 | — | 7.56 | — |
| 6 hrs | 7.72 | — | 7.64 | — | 7.62 | — | 7.62 | — |
| 22 hrs | 8.23 | 3+ | 8.30 | — | 8.30 | — | 8.28 | — |
| 24 hrs | 8.30 | 3+ | 8.36 | — | 8.38 | — | 8.35 | — |
| 27 hrs | 8.40 | 3+ | 8.42 | — | 8.42 | — | 8.40 | — |
| 30 hrs | 8.45 | 3+ | 8.47 | Flotage± | 8.49 | — | 8.46 | — |
| 46 hrs | 8.70 | 3+ | 8.56 | 3+ | 8.70 | — | 8.69 | — |
| 48 hrs | 8.76 | 3+ | 8.60 | 3+ | 8.73 | — | 8.71 | — |

(5. Consideration)

From the results shown in Tables 9 and 10 above, it is understood that the formation of precipitates is significantly prevented by incorporation of phosphate ion into the drug solution. Even at such a low monophosphate concentration as 0.1 mEq/L as an inorganic phosphorous concentration (0.31 mg/dL), it is recognized that the precipitate formation is prevented to a certain extent.

In addition to the above, another comparative test was carried out using a drug solution not containing phosphate ion and a drug solution containing monophosphate ion at 4 mg/dL as an inorganic phosphorous concentration. Nearly linear rise of the pH from 7.23-7.29 to 7.89-7.94 was observed within 7 days, during which the particle size and number of insoluble fine particles increased significantly in the drug solution not containing phosphate ion but such increase was substantially not observed in the drug solution containing phosphate ion in spite of the pH rise as above.

INDUSTRIAL APPLICABILITY

According to the invention, there is provided a drug solution to be mixed on use which comprises sodium bicarbonate incorporated with phosphate ion. There is also provided a dialysate or substitution liquid for acute blood purification, especially a dialysate or substitution liquid for acute blood purification which does not cause hypokalemia and hypophosphatemia. There is further provided a dialysate or substitution liquid to be mixed on use for acute blood purification which is prevented from production of insoluble fine particles or precipitates over a long period of time after mixing.

The invention claimed is:

1. A drug solution for acute blood purification comprising:
sodium ions; potassium ions; chloride ions; bicarbonate ions; calcium ions; magnesium ions; monophosphate ions, and glucose, but comprising no acetate ions and no citrate ions,
wherein the drug solution has
a concentration of the sodium ions in a range from 132 to 143 mEq/L,
a concentration of the potassium ions in a range from 3.5 to 5.0 mEq/L,
a concentration of the chloride ions in a range from 104 to 114.5 mEq/L,
a concentration of the bicarbonate ions in a range from 32 to 35 mEq/L,
a concentration of the calcium ions in a range from 2.5 to 3.5 mEq/L,
a concentration of the magnesium ions in a range from 1 to 1.5 mEq/L, and
a concentration of the monophosphate ions in a range from 2.3 to 4.5 mg/dL,
wherein the concentration of the monophosphate ions is calculated as an inorganic phosphorus concentration.

2. The drug solution according to claim 1, wherein production of insoluble fine particles or precipitates in the drug solution does not occur even after pH of the drug solution rises to 7.5 or more.

3. The drug solution according to claim1, which does not cause hypokalemia or hypophosphatemia.

4. The drug solution according to claim 1, which is tolerated by a patient having acetate intolerance.

5. The drug solution according to claim 1, which retains a monophosphate ion concentration in plasma without a variation more than 17% over 24 hours from a beginning of an acute blood purification therapy by administering the drug solution to a mammal, which includes a human, as a dialysate or substitution liquid.

6. A method of removing unnecessary or toxic substances from blood in a subject in need of acute blood purification, comprising:
performing the acute blood purification, which continuously purifies the blood of the subject; and
simultaneously administering a drug solution to the blood of the subject continuously,
wherein the drug solution comprises sodium ions, potassium ions, chloride ions, bicarbonate ions, calcium ions, magnesium ions, monophosphate ions, and glucose, but comprising no acetate ions and no citrate ions,
wherein the drug solution has
a concentration of the sodium ions in a range from 132 to 143 mEq/L,
a concentration of the potassium ions in a range from 3.5 to 5.0 mEq/L,
a concentration of the chloride ions in a range from 104 to 114.5 mEq/L,
a concentration of the bicarbonate ions in a range from 32 to 35 mEq/L,
a concentration of the calcium ions in a range from 2.5 to 3.5 mEq/L,
a concentration of the magnesium ions in a range from 1 to 1.5 mEq/L, and
a concentration of the monophosphate ions in a range from 2.3 to 4.5 mg/dL,
wherein the concentration of the monophosphate ions is calculated as an inorganic phosphorus concentration.

7. The drug solution according to claim 1, wherein the drug solution comprises:
the sodium ions of 138 mEq/L;
the potassium ions of 4 mEq/L;
the chloride ions in a range from 111 to 112.2 mEq/L;
the bicarbonate ions of 32 mEq/L;
the calcium ions of 2.5 mEq/L;
the magnesium ions of 1 mEq/L; and
the monophosphate ions of 4 mg/dL,
wherein the concentration of the monophosphate ions is calculated as an inorganic phosphorus concentration.

8. The method according to claim 6, wherein the drug solution comprises:
the sodium ions of 138 mEq/L;
the potassium ions of 4 mEq/L;
the chloride ions in a range from 111 to 112.2 mEq/L;
the bicarbonate ions of 32 mEq/L;
the calcium ions of 2.5 mEq/L;
the magnesium ions of 1 mEq/L; and
the monophosphate ions of 4 mg/dL,
wherein the concentration of the monophosphate ions is calculated as an inorganic phosphorus concentration.

* * * * *